United States Patent [19]

Lucas et al.

[11] Patent Number: 5,017,879
[45] Date of Patent: May 21, 1991

[54] CAPACITIVE VOID FRACTION MEASUREMENT APPARATUS

[75] Inventors: Gary Lucas, Fieldside; Maurice Beck, Altrincham; Andrew Hunt, Orwell, all of England

[73] Assignee: Schlumberger Technology Corporation, Houston, Tex.

[21] Appl. No.: 408,451

[22] Filed: Sep. 15, 1989

Related U.S. Application Data

[63] Continuation of Ser. No. 243,527, Sep. 12, 1988, abandoned.

[30] Foreign Application Priority Data

Sep. 17, 1987 [GB] United Kingdom ............... 8721858

[51] Int. Cl.⁵ .............................................. G01R 27/26
[52] U.S. Cl. ..................................... 324/663; 324/686
[58] Field of Search .................. 324/61 R, 61 P, 663, 324/686, 687, 688

[56] References Cited

U.S. PATENT DOCUMENTS

| | | | |
|---|---|---|---|
| 2,976,720 | 3/1961 | Callahan | 324/61 R |
| 3,639,835 | 2/1972 | Dammig, Jr. et al. | 324/61 R |
| 4,074,184 | 2/1978 | Dechene et al. | 324/61 R |
| 4,082,994 | 4/1978 | Newton | 324/438 |
| 4,288,741 | 9/1981 | Dechene et al. | 324/61 R |
| 4,713,603 | 12/1987 | Thorn | 324/61 P |
| 4,899,101 | 2/1990 | Porges | 324/663 |

FOREIGN PATENT DOCUMENTS

| | | | |
|---|---|---|---|
| 8502016 | 5/1985 | European Pat. Off. | |
| 3049035 | 7/1982 | Fed. Rep. of Germany. | |
| 548798 | 3/1977 | U.S.S.R. | 324/61 R |
| 566174 | 7/1977 | U.S.S.R. | 324/61 R |
| 878712 | 10/1961 | United Kingdom. | |

OTHER PUBLICATIONS

J. Phys. E: Scientific Instruments, vol. 11, 12/1978, Printed in Great Britain, "A Low-Cost Solids Flowmeter for Industrial Use", pp. 1005-1009.

"A Frequency-Modulated Capacitance Transducer for On-Line Measurement of Two-Component Fluid Flow", by R. G. Green and J. M. Cunliffe, 8252 Measurement 1 (1983), Oct.-Dec., No. 4, London, Gr. Britain.

Abstract-"Method and Apparatus for Measuring Average Void Ratio of Flowline of Gas-Liquid Two-Phase Stream", by Nobuo Yamamoto, vol. 10, No. 72 (P-438) (2129), Mar. 22, 1986.

*Primary Examiner*—Kenneth Wieder
*Assistant Examiner*—Maura K. Regan
*Attorney, Agent, or Firm*—Henri DuPont; Martin Hyden; John J. Ryberg

[57] ABSTRACT

An apparatus for use in the capacitive measurement of the void fraction in a flowing liquid. An assembly of at least two electrodes is spaced apart around the exterior of the body defining a flow passage such that the capacitance of the electrode assembly is a function of the dielectric constant of material within the passageway. The radial thickness of the body is substantial such that the passageway occupies a portion of the electrostatic field of the electrode assembly which is relatively uniform. The dielectric constant of the body may be substantially equal to the expected dielectric constant of the said liquid. The body may be tubular with the electrode assembly directly supported on the radially outer surface of the tube.

21 Claims, 6 Drawing Sheets

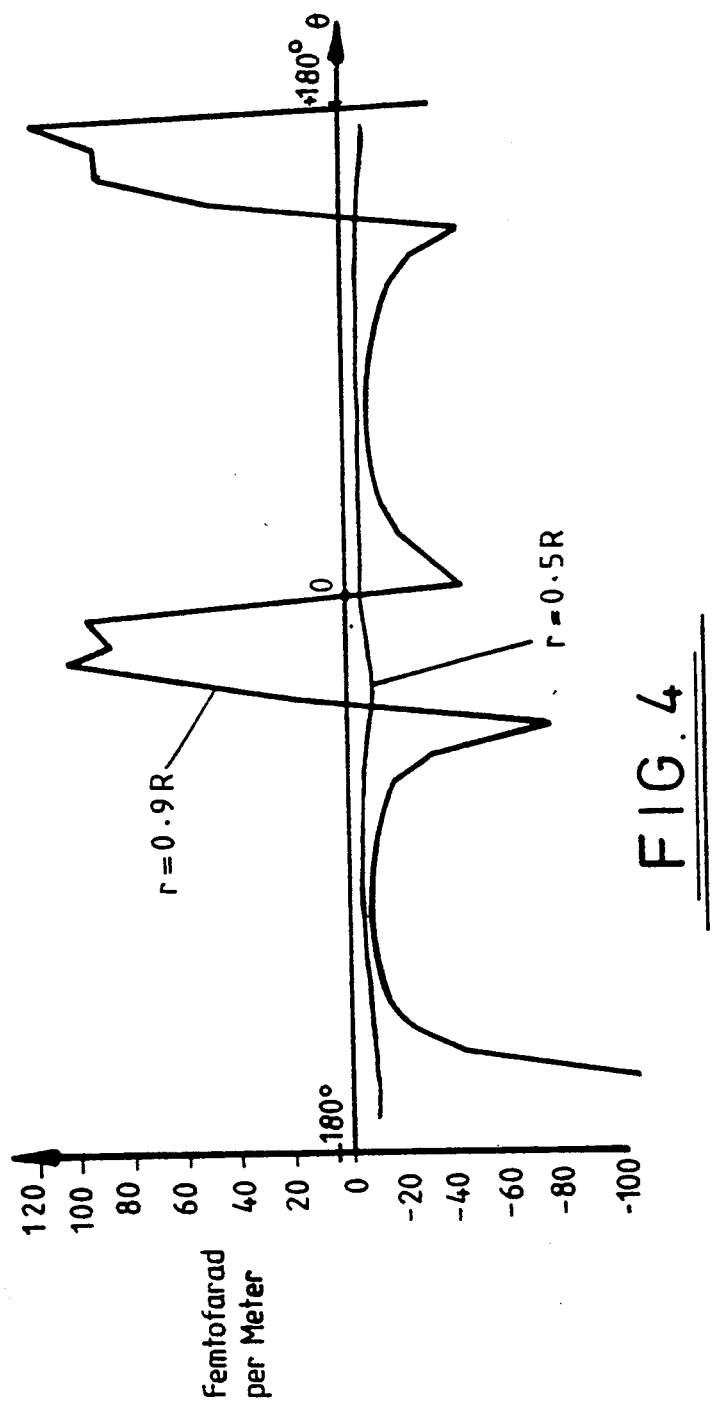

CAPACITIVE VOID FRACTION MEASUREMENT APPARATUS

This is a continuaction of application Ser. No. 071243, S27 filed Sept. 12, 1988, now abandoned.

The present invention relates to a capacitive void fraction measurement apparatus.

There are numerous circumstances in which it is desirable to be able to measure the void fraction in a flowing liquid. For example, product flowing from an oil well is often in two phases, that is oil and natural gas, and it is necessary for efficient control of the oil well to be able to monitor the downhole gas content of the product. The gas content is generally defined as the "void fraction", which term is used herein to mean the ratio of the volume of bubbles of vapour in a flowing liquid to the volume of that liquid.

Various attempts have been made in the past to measure the mean void fraction of two phase bubbly liquid flows using capacitive sensors. It has however been found that the electrostatic fields generated by the known sensors and through which the liquid to be monitored flows are not uniform. This means that the change in the capacitance of the sensor resulting from a particular gas bubble is highly dependent upon the position of that bubble relative to the electrostatic field. As a consequence the response of the known sensors is greatly influenced by the local void fraction distribution.

Various researchers have reported that the local void fraction distribution in a two phase gas-liquid flow is influenced by the overall flow pattern and that the void fraction distribution significantly influences the output of conventional void fraction sensors. For example, the article "Turbulence structure of air-water bubbly flow II. Int. J. Multiphase Flow; Vol. 2" by Serizawa, A. and Michiyoshi, I. (1975) reported that in two phase flows the local void fraction distribution is a strong function of the overall flow pattern and can therefore be influenced by such factors as the mean void fraction and the liquid superficial velocity. In a Ph. D. thesis by Bernier, R. J. N. (1981) made available at the California Institute of Technology a series of experiments is reported using vertically upward two phase flows which showed that the variation of the output of an impedance void fraction sensor with mean void fraction was influenced by the local void fraction distribution. A further Ph. D thesis by Hammer, E. A. (1983) made available at the University of Manchester Institute of Science and Technology reports a series of experiments using vertically upward two phase flows monitored by a capacitance noise sensor. The experiments showed that for a given value of the mean void fraction of the flow the output from the sensor was influenced by the liquid superficial velocity which in turn suggests that the capacitance sensors used were susceptible to variations in the local void fraction distribution.

In view of the above research results it would clearly be desirable to develop a void fraction sensor which is not sensitive to variations in the local void fraction distribution. It is accordingly an object to the present invention to provide such a sensor.

According to the present invention there is provided an apparatus for use in the capacitive measurement of the void fraction in a flowing liquid, comprising a body defining a flow passage through which in use the said liquid flows, and an assembly of at least two electrodes spaced apart around the exterior of the body or embedded in the body, the material of the body and the disposition of the electrodes being such that the capacitance of the electrode assembly is a function of the dielectric constant of material within the passageway, wherein the radial thickness of the body is substantial such that the passageway occupies a portion of the electrostatic field of the electrode assembly which is relatively uniform.

The radial thickness of the body may be determined such that the ratio of the standard deviation of the electrostatic field sensitivity divided by its mean value is no more than 1.

Preferably, the dielectric constant of the body is substantially equal to the expected dielectric constant of the said liquid. The body may be tubular and support the electrode assembly on its radially outer surface. Preferably, the radial thickness of the body is at least 30% of the radius of the radially outer surface of the body.

The electrode assembly may comprise two capacitor electrodes arranged on diametrically opposite sides of the tubular body, and two earthed electrodes positioned on diametrically opposite sides of the tubular body between the capacitor electrodes. Each of the capacitor electrodes preferably subtends an angle of substantially 144° at the axis of the tubular body.

In an alternative arrangement the capacitor electrodes are shaped such that their middles (in the circumferential direction) are closer to the flow passage than their edges.

The body may be formed from polytetrafluoro-ethylene (hereinafter referred to as PTFE).

An embodiment of the present invention will now be described, by way of example, with reference to the accompanying drawings, in which:

FIG. 4 illustrates variations in the capacitance of the sensor of FIG. 3 with variations in the void fraction distribution for a single bubble placed at various positions in the pipe;

Figure 1:
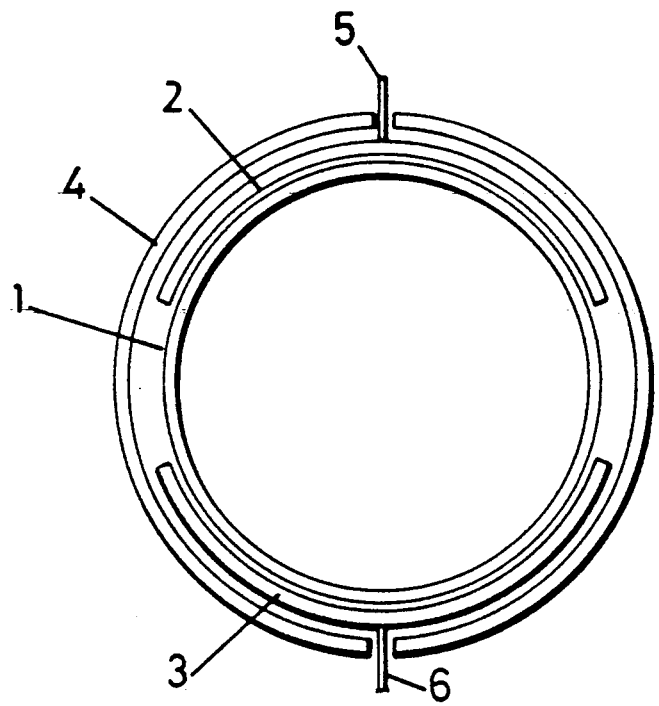
FIG. 1 is a schematic sectional illustration of a conventional void fraction capacitive sensor.

Referring to FIG. 1, the conventional illustrated capacitive sensor comprises a tube 1 through which flows a two phase fluid such as oil containing natural gas bubbles. Supported on the outer surface of the tube 1 is a first electrode 2 to which an excitation signal is applied and a second electrode 3 which is a virtual earth measuring electrode. The electrode assembly is housed within a cylindrical electrostatic shield 4 which is penetrated by electrical leads 5 and 6.

Figure 2:
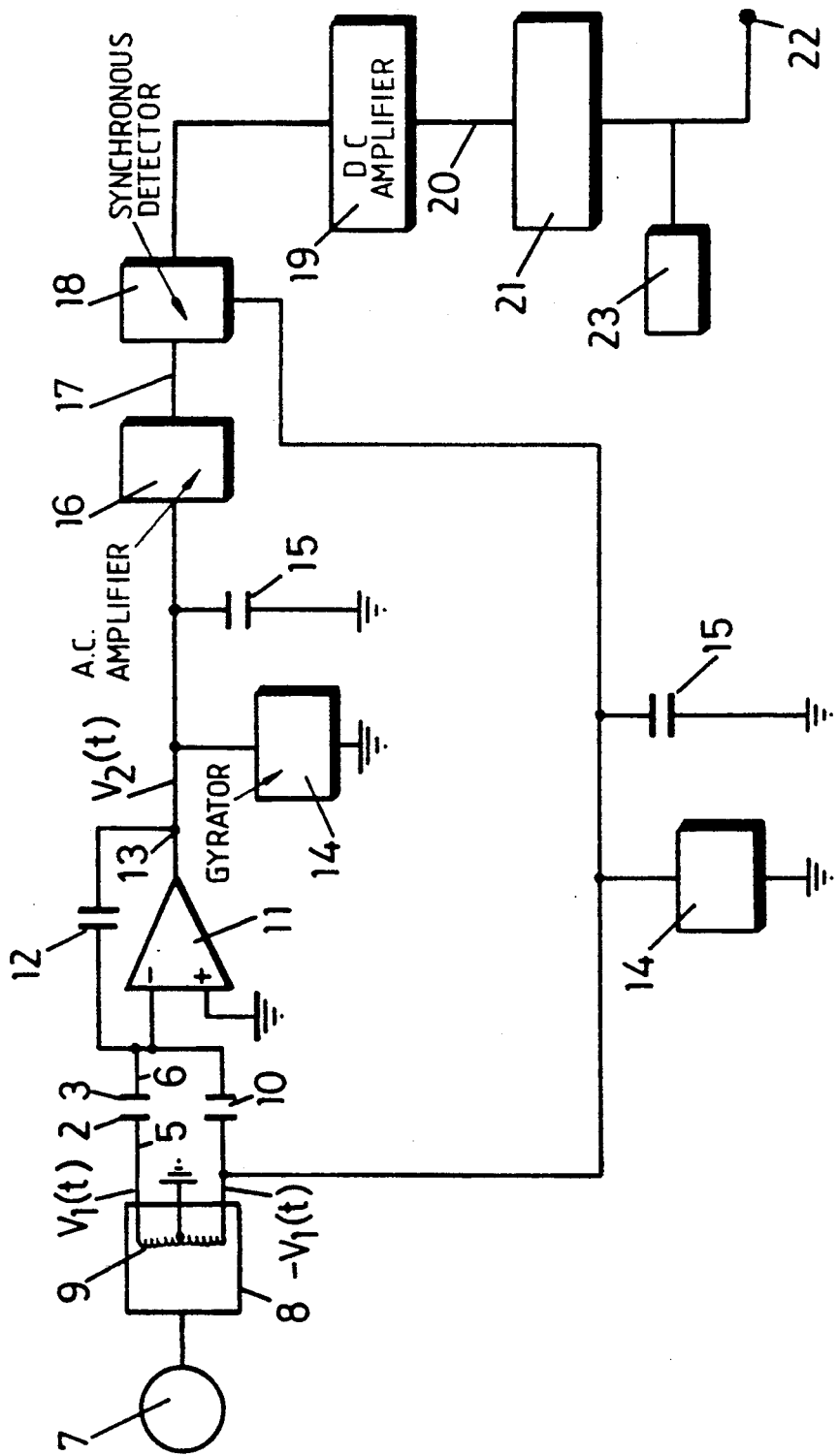
FIG. 2 is a schematic circuit diagram of a capacitance measurement circuit which may be used with the conventional sensor illustrated in FIG. 1 or sensors in accordance with the present invention.

Referring now to FIG. 2, a circuit to which the sensor assembly of FIG. 1 is connected is illustrated. A 10 kHz oscillator 7 applies an excitation signal $V_1$ to a transformer 8 which has a secondary winding 9 producing outputs which are 180° out of phase with each other. One of these outputs is applied to the electrical lead 5 of the assembly of FIG. 1 and the other output is applied to a reference capacitor 10. The capacitance of the reference capacitor 10 is substantially the same as the capacitance of the assembly illustrated in FIG. 1. The lead 6 of the assembly of FIG. 1 and the capacitor 10 are connected to an amplifier 11. A capacitor 12 provides a feedback circuit for the amplifier 11 such that the signal $V_2(t)$ appearing at the output 13 of the amplifier is as follows:

$$V_2(t) = V_1(t)(C_x - C_{ref})/C_{fb}$$

where $V_1(t)$ is the signal applied to lead 5
$C_x$ is the capacitance of the sensor
$C_{ref}$ is the capacitance of capacitor 10
$C_{fb}$ is the capacitance of the capacitor 12.

The signal on output 13 is passed via a bandpass filter, comprising an inductor or a gyrator 14 in parallel with a capacitor 15, to an AC amplifier 16. The gyrator 14 acts as a passive inductance and may be of conventional form comprising for example a type 353 operational amplifier, four resistors and a capacitor. The AC amplifier 16 provides a modulation input 17 to a synchronous detector 18. The synchronous detector also receives the signal applied to the capacitor 10 via a further bandpass filter comprising gyrator 14 and capacitor 15 which are identical to the like-numbered components connected to output 13. The two bandpass filters are tuned to the supply frequency 10 kHz. The synchronous detector 18 extracts the DC component of the output of the amplifier 16 and this is applied to a DC amplifier 19.

The output 20 of the amplifier 19 is passed through a low pass filter 21 to remove any residual 10 kHz signal. The resultant DC signal is applied to output terminal 22, a zero adjust circuit 23 being provided to calibrate the output 22. For example the circuit 23 can be used to adjust the output to zero when it is known that there are no bubbles between the electrodes 2 and 3 of the measurement capacitor assembly illustrated in FIG. 1.

The circuit of FIG. 2 can be used in association with a conventional sensor arrangement of the type illustrated in FIG. 1 or any other capacitive sensor, including the sensor in accordance with the present invention described in detail below.

The electrode assembly illustrated in FIG. 1 is such that gaps are left between the adjacent edges of the electrodes 2 and 3. To ensure that no stray fields could influence the space within the flow tube an electrode assembly of the type illustrated in FIG. 3 was produced in which earthed electrodes 24 and 25 were positioned between the excitation electrode 2 and the measuring electrode 3. In other respects the electrode structure was exactly the same as that illustrated in FIG. 1 and the electrode structure was connected to the circuit of FIG. 2. The effect of variations in the void fraction distribution was then investigated, bubbles being introduced into the tube at positions indicated by an angle $\theta$ measured from a datum angular position and a radial position r. The internal radius of the electrodes is indicated as R.

Figure 3:
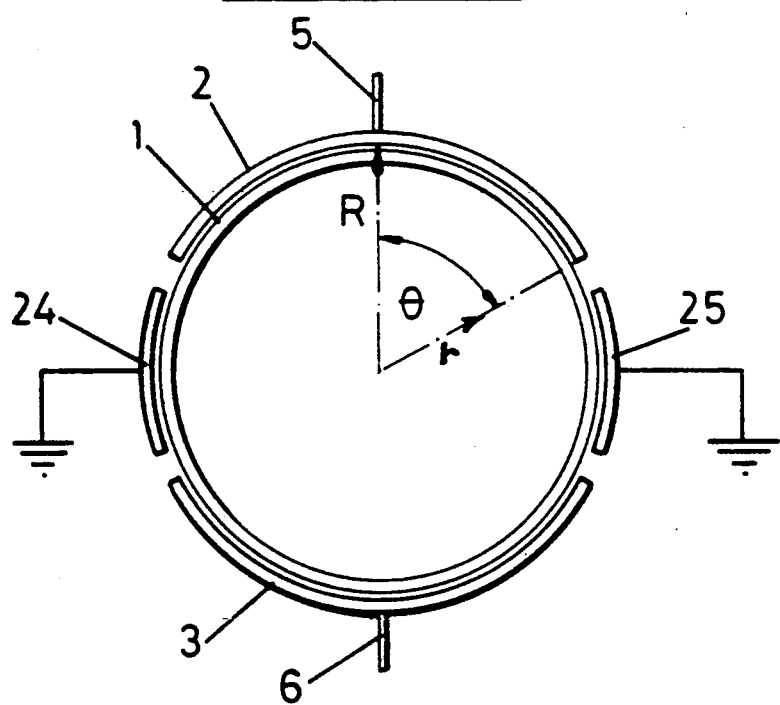
FIG. 3 is a schematic sectional view of a capacitive sensor electrode structure used experimentally to investigate the variation in capacitance with void fraction distribution.

Referring to FIG. 4, a plot of the variation in the measured capacitance of the electrode assembly of FIG. 3 is shown for bubbles located at $r=0.9R$, and $r=0.5R$ as a function of $\theta$. It can be seen that there are very large fluctuations in the measured capacitance for the same size of bubble depending on the angular position of the bubble when the bubble is close to the electrodes. When the bubble is not close to the electrodes however, the angular position of the bubble has little effect on the measured change in capacitance. Accordingly it is clear that the electrostatic field is relatively uniform towards the centre of the flow passageway defined by the electrodes but becomes progressively less uniform towards the electrodes. In order to provide a measure of the uniformity of the electrostatic field produced by given boundary electrode arrangement the following technique was adopted:

An electrode radius of 50 mm is assumed, and the region inside the electrodes is divided up into a series of rings or annuli. The mean radius of the $i^{th}$ annulus is $r_i$ whilst the distance between the inner and outer radii of each annulus is 2d. A working radius $r_w$ is defined, and a weighted mean capacitance charge term $(\overline{Y})_{rw}$ is defined for the region within the working radius, such that:

$$(\overline{Y})_{rw} = \left[ \sum_{r_i=r_1}^{r_i=r_w-d} A_{ri}\overline{(\Delta C)}_{ri} \right] \frac{1}{\left[ \sum_{r_i=r_1}^{r_i=r_w-d} A_{ri} \right]}$$

Here, $\overline{(\Delta C)}_{ri}$ represents the means value of $\Delta C$ within the $i^{th}$ annulus. It should be noted that the values of $\Delta C$, used in the determination of $\overline{(\Delta C)}_{ri}$, are computed for the case where the radial co-ordinate of the bubble is assumed fixed at a value of $r_i$ whilst its angular co-ordinate $\theta$ assumes values in the range of $+180°$ to $-180°$. The term $A_{ri}$ in the above equation, represents the cross sectional area of the $i^{th}$ annulus.

A weighted atandard deviation term $\overline{(\sigma)}_{rw}$ can also be defined for the region within the working radius; thus, $$(\overline{\sigma})_{rw} = \sqrt{\left[ \sum_{r_i=r_1}^{r_i=r_w-d} A_{ri}(\sigma_{ri})^2_{rw} \right] \frac{1}{\left[ \sum_{r_i=r_1}^{r_i=r_w-d} A_{ri} \right]}}$$

Here $(\sigma_{ri})^2_{rw}$ represents the variance of the parameter $\Delta C$ in the $i^{th}$ annulus, assuming a mean value for $\Delta C$ of $(e, ovs/Y/)_{rw}$.

It is possible to define a term $z_{rw}$ such that:

$$Z_{rw} = \left| \frac{\overline{(\sigma)}_{rw}}{\overline{(Y)}_{rw}} \right|$$

$z_{rw}$ is a measure of the uniformity of that portion of the electrostatic field (produced by a given boundary electorde arrangement) which resides within the working radius $r_w$. Thus a relatively low value of $z_{rw}$ indicates that the electrostatic field within the working radius is relatively uniform. Conversely, a high value of $z_{rw}$ indicates the existence of a relatively non-uniform electrostatic field within the working radius.

Figure 5:
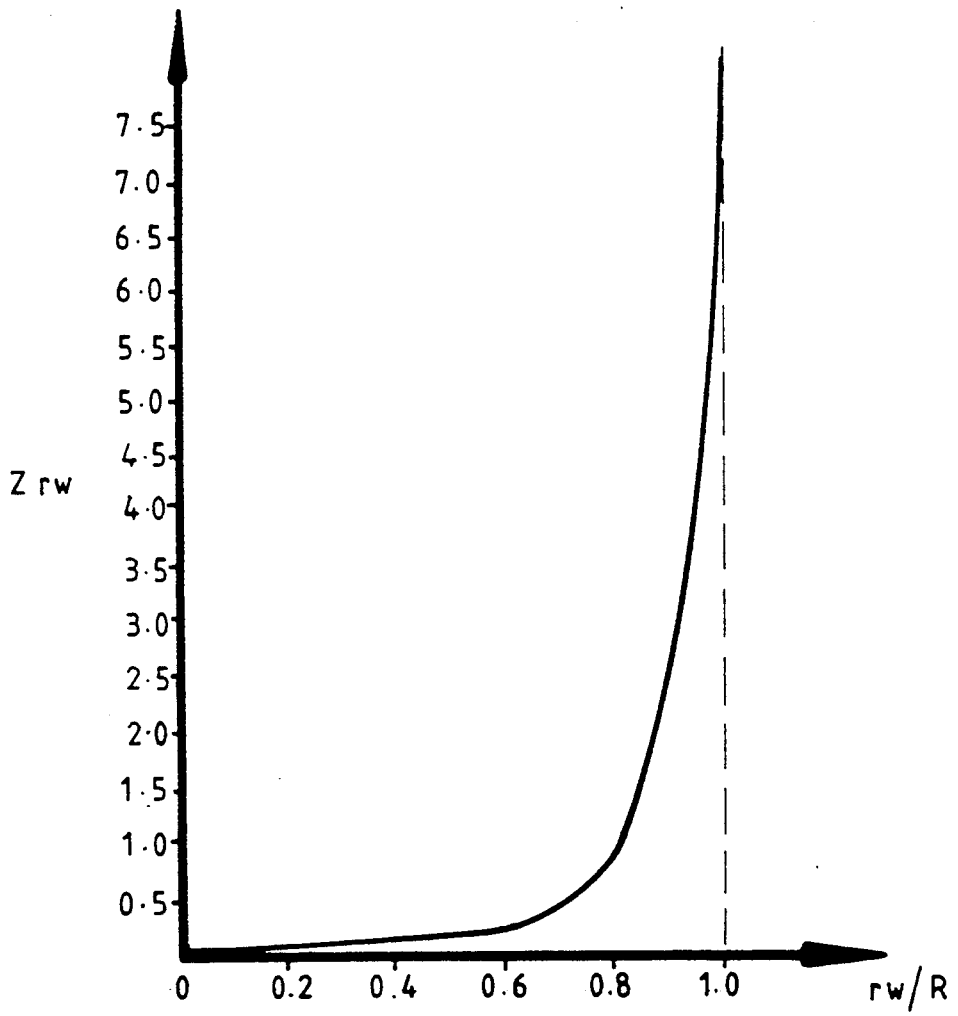
FIG. 5 illustrates the variation of a measure of the uniformity of the electrostatic field produced by the electrode assembly illustrated in FIG. 3 with variation of the radial position.

A plot of $z_{rw}$ versus $r_w/R$ (where R is the electrode radius) for the boundary electrode arrangement illustrated in FIG. 3 is shown in FIG. 5. It is clear from this figure that $Z_{rw}$ is strongly dependent upon the value of $r_w/R$.

In addition, it has been shown that the boundary electrode arrangement has a weak influence on the variation of $Z_{rw}$ with $r_w/R$. On the assumption that the optimum boundary electrode arrangement is that which gives rise to the lowest values of $Z_{rw}$ at the relevant values of $r_w/R$, it has been found that the optimum boundary electrode arrangement consists of;

(i) A single 144° excitation electrode (2, FIG. 3);

(ii) Two 36° excitation electrodes (24, 25, FIG. 3) which are held at earth potential; and (iii) A single 144° virtual earth electrode (3, FIG. 3).

The curve of FIG. 5 shows the variation of $Z_{rw}$ with $r_w/R$ for this electrode arrangement.

It is apparent from FIG. 5 that the sensor capacitance is largely independent of bubble distribution providing the bubbles are kept out of the region adjacent to the capacitor electrodes. In accordance with the present invention this can be achieved if all the fluid flow is confined within a region the radius of which is substantially less than the radius of the capacitor electrode. The sensor assembly in accordance with the invention is illustrated in FIGS. 6 and 7.

Figure 6:
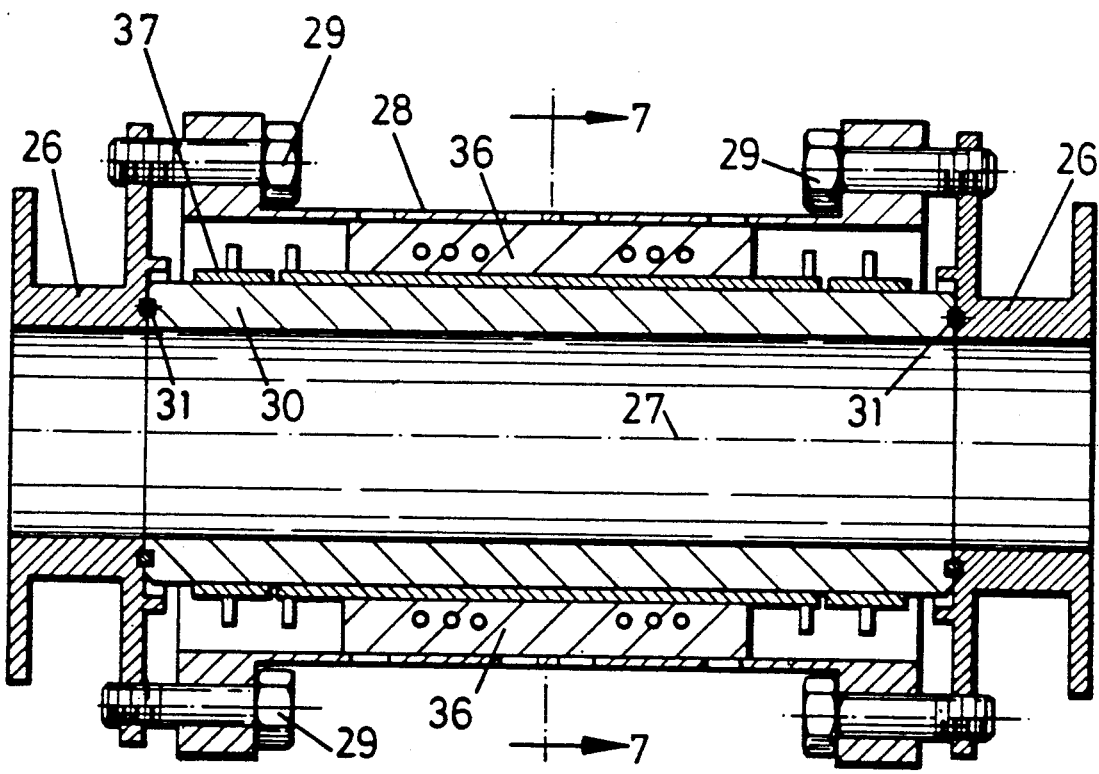
FIG. 6 is a sectional view of a capacitive void fraction sensor in accordance with the present invention.
Figure 7:
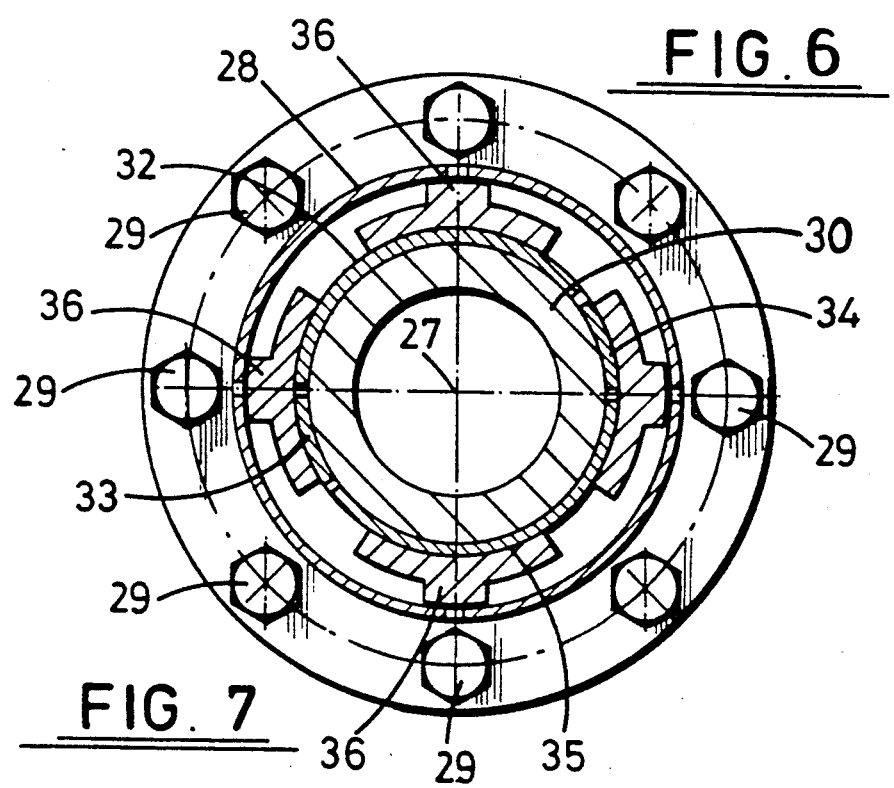
FIG. 7 is a section on the line 7—7 of FIG. 6.

Referring to FIG. 6, this shows a section drawn through a capacitive sensor which is intended to be connected by flanges 26 in a pipe carrying for example a mixture of oil and natural gas. The pipe axis is indicated by dotted line 27.

The sensor comprises a tubular aluminium shield 28 secured by bolts 29 to the end flanges 26. Tension in the bolts 29 compresses the end flanges against a tubular PTFE body 30, the ends of the PTFE body 30 being sealed by O-rings 31 against the end flanges 26. The PTFE body 30 supports four electrodes as best shown in FIG. 7, that is an electrode 32 corresponding to the electrode 2 of FIG. 3 and to which an excitation signal is applied, electrodes 33 and 34 which are connected to earth and correspond to the electrodes 24 and 25 of FIG. 3, and an electrode 35 which is the measuring capacitor and corresponds to the electrode 3 of FIG. 3. The electrodes 32 and 35 subtend an angle of 144° at the axis 27 whereas the electrodes 33 and 34 each subtend an angle of 36°. Insulating spacers 36 are secured between the shield 28 and the electrode assembly. Conventional guard electrodes 37 are positioned at each axial end of each of the electrodes and driven by appropriate signals so as to minimise end effects.

The inner radius of the PTFE tubular body 30 is selected to correspond to the radius of the pipeline into which the sensor is introduced. The outer radius is selected such that the tubular body itself occupies that region of the electrostatic field generated between the electrodes 32 and 35 which is significantly non-uniform. Depending on the particular application different degrees of uniformity might be required to provide the required measurement accuracy. In the case of the embodiment illustrated in FIGS. 6 and 7, the radial thickness of the PTFE tube 30 was selected to correspond to 30% of the radial distance from the axis 26 to the radially inner surface of the electrode structure. Referring to the curve in FIG. 5 it will be seen that this corresponds to a $Z_{rw}$ value of less than 0.5. If a greater uniformity were required it would of course be possible to increase the relative thickness of the PTFE tube so that it occupied more than 30% of the radius of the electrode structure. Equally a thinner tube would be appropriate if a less uniform field was acceptable. Experiments have shown however that the ratio of the thickness of the PTFE tube of the embodiment illustrated in FIGS. 6 and 7 is sufficient to provide an acceptable uniformity in an oil/natural gas application.

In the arrangement of FIGS. 6 and 7 the tubular body 30 is fabricated from PTFE. This has a dielectric constant of approximately 2.1 which is similar to the dielectric constant of oil. Ideally the dielectric constant of the tubular body 30 will be identical to the dielectric constant of the fluid passing therethrough, that is the combination of the oil and the gas bubbles entrained therein. The closer the correspondence beween the dielectric constant of the tubular body 30 and the fluid which flows therethrough the better as this reduces the distortion of the electrostatic field within the tube 30 resulting from the presence of the tube. The invention does however provide substantial advantages even if the dielectric constant of the tube 30 differs from that of the fluid passing therethrough. If the dielectric constant of the tube 30 is too high however it effectively negates the spacing between the electrode structure and the periphery of the flow channel. Preferably therefore the dielectric constant of the tube 30 is fairly small, for example 5 or less.

It will of course be appreciated that any material with an appropriate dielectric constant can be used for the tube 30.

Experiments have been conducted with a sensor of the type described with reference to FIG. 6 and 7 in which the sensor axis (27) was vertical. The fluid passing through the sensor was a mixture of mineral oil and air bubbles. The variation in the output of the capacitance sensor with the mean flow void fraction was measured over a range of superficial liquid velocities. It was found that the variation in the output of the sensor with the mean flow void fraction was linear and was relatively insensitive to the oil superficial velocity. This indicates that the sensor was relatively unaffected by the minor variations in the local void fraction distribution which occurred as the oil superficial velocity was varied.

A further series of experiments was performed on the capacitance void sensor in flows that were deviated from the vertical. Such flows are commonly encountered in downhole oilwell monitoring applications. In deviated flows, gross changes in the local void fraction distribution occur due to large buoyancy forces acting on the gas bubbles. It was found that, at a given mean void fraction of the flow, the output from the capacitance sensor was influenced by the angle of deviation of the flow. This influence was however predictable and could be compensated for.

Figure 8:
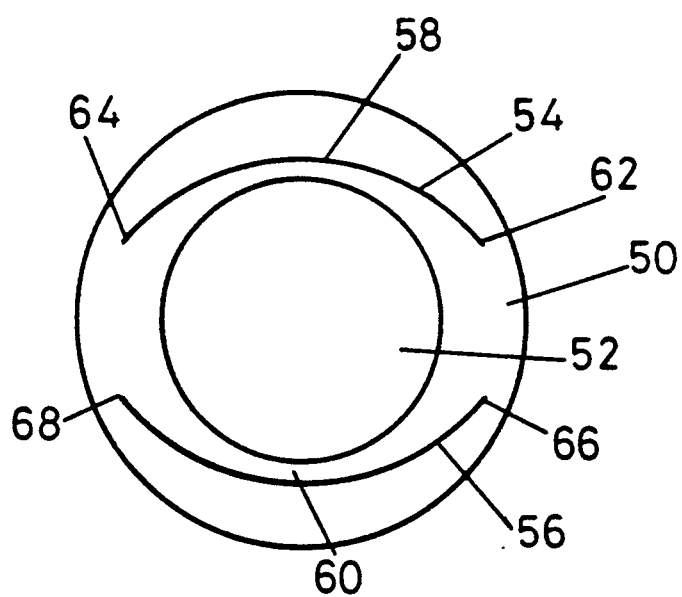
FIG. 8 is a sketch of a cross-section of a second embodiment of the invention, the section being perpendicular to the longitudinal axis of the sensor.

In the embodiment of the apparatus of the invention shown in FIG. 8, the body 50 defining a flow passage 52 has an annular cross-section and is made of a material having a dielectric constant substantially equal to the expected dielectric constant of the liquid flowing through the flow passage 52. The device comprises two identical electrodes 54 and 56 facing each other and embedded in the body 50. They have a rounded shape. The middle 58 or 60 of each electrode is located nearer to the flow passage than the edges 62-64 or 66-68 which are set back into the body 50. In this embodiment, the flow passage is further away from the edges of the electrodes where the sensitivity of the electrostatic field is highly non-uniform, as is apparent from FIG. 4. Guard electrodes could be added, as in FIG. 3, following the same principle.

We claim:

1. An apparatus for use in the capacitive measurement of the void fraction in a flowing liquid, comprising:
   a body defining a flow passage through which said liquid flows, said body having a radial thickness and a dielectric constant which is substantially equal to the expected dielectric constant of said liquid; and
   electrodes supported by said body for producing an electrostatic field within said flow passage, whereby measurement of the capacitance between said electrodes is indicative of the void fraction of said liquid, said radial thickness, of said body having been varied to a set predetermined radial thickness, whereby predetermining said thickness results in a substantially uniform electrostatic field within said flow passage.

2. The apparatus defined in claim 1, wherein said electrodes are shaped such that their middles are located nearer to the flow passage than their edges.

3. The apparatus defined in claim 1 wherein said body is tubular and said electrodes are directly supported on the radially outer surface of said body.

4. The apparatus defined in claim 3 wherein the radial thickness of said body is at least 30% of the radius of the radially outer surface of said body.

5. The apparatus defined in claim 3 wherein said electrodes comprise two capacitor electrodes arranged on diametrically opposite sides of the tubular body, and two grounded electrodes positioned on diametrically opposite sides of the tubular body between the capacitor electrodes.

6. The apparatus defined in claim 5 wherein each of said capacitor electrodes subtends an angle of substantially 144° and each of the grounded electrodes subtends an angle of substantially 36° at the axis of the tubular body.

7. The apparatus defined in claim 1 wherein said body is formed from polytetrafluoroethylene.

8. The apparatus defined in claim 1 wherein said electrodes are embedded in said body.

9. The apparatus defined in claim 1 wherein said substantially uniform electrostatic field is obtained when the ratio of the standard deviation of the electrostatic field sensitivity within said passage divided by its mean value is less than or equal to one.

10. An apparatus for use in the capacitive measurement of the void fraction in a flowing liquid, comprising:
    a body defining a flow passage through which said liquid flows; and
    electrodes supported by said body for producing an electrostatic field within said flow passage, whereby measurement of the capacitance between said electrodes is indicative of the void fraction of said liquid, said body having a dielectric constant which is substantially equal to the expected dielectric constant of said liquid.

11. The apparatus defined in claim 10 wherein said electrodes are shaped such that their middles are located nearer to the flow passage than their edges.

12. The apparatus defined in claim 10 wherein said body is tubular and said electrodes are directly supported on the radially outer surface of said body.

13. The apparatus defined in claim 12 wherein said electrodes comprise two capacitor electrodes arranged on diametrically opposite sides of the tubular body, and two grounded electrodes positioned on diametrically opposite sides of the tubular body between the capacitor electrodes.

14. The apparatus defined in claim 12 wherein each of said capacitor electrodes subtends an angle of substantially 144° and each of the grounded electrodes subtends an angle of substantially 36° at the axis of the tubular body.

15. An apparatus for use in the capacitive measurement of the void fraction in a flowing liquid, comprising:
    a body defining a flow passage through which said liquid flows; and
    electrodes supported by said body for producing an electrostatic field within said flow passage, whereby measurement of the capacitance between said electrodes is indicative of the void fraction of said liquid, said body having side walls with a dielectric constant and a radial thickness, the value of the dielectric constant being chosen with respect to the expected dielectric constant of said liquid and said radial thickness having been varied to a set predetermined thickness, whereby predetermining said radial thickness results in a substantially uniform electrostatic field within said flow passage.

16. The apparatus defined in claim 15 wherein the dielectric constant of said body is substantially equal to the expected dielectric constant of said liquid.

17. The apparatus defined in claim 15 wherein the radial thickness of said side walls of said body is at least 30% of the radius of the radially outer surface of said body.

18. The apparatus defined in claim 15 wherein said body is tubular and said electrodes comprise two capacitor electrodes arranged on diametrically opposite sides of the tubular body, and two grounded electrodes positioned on diametrically opposite sides of the tubular body between the capacitor electrodes.

19. The apparatus defined in claim 15 wherein said electrodes are shaped such that their middles are located nearer to the flow passage than their edges.

20. The apparatus defined in claim 15 wherein said body is formed from polytetrafluoroethylene.

21. The apparatus defined in claim 15 wherein said substantially uniform electrostatic field is obtained when the ratio of the standard deviation of the electrostatic field sensitivity within said passage divided by its mean value is less than or equal to one.

* * * * *